(12) United States Patent
Maher

(10) Patent No.: US 9,611,194 B2
(45) Date of Patent: Apr. 4, 2017

(54) SIMULATED MOVING BED SEPARATORS AND METHODS FOR ISOLATING A DESIRED COMPONENT

(71) Applicant: UOP LLC, Des Plaines, IL (US)

(72) Inventor: Gregory F. Maher, Aurora, IL (US)

(73) Assignee: UOP LLC, Des Plaines, IL (US)

( * ) Notice: Subject to any disclaimer, the term of this patent is extended or adjusted under 35 U.S.C. 154(b) by 260 days.

(21) Appl. No.: 14/460,740

(22) Filed: Aug. 15, 2014

(65) Prior Publication Data

US 2016/0046545 A1    Feb. 18, 2016

(51) Int. Cl.
*C07C 7/13* (2006.01)
*C07C 7/00* (2006.01)
*B01D 15/18* (2006.01)

(52) U.S. Cl.
CPC .......... *C07C 7/005* (2013.01); *B01D 15/1835* (2013.01); *C07C 7/13* (2013.01)

(58) Field of Classification Search
None
See application file for complete search history.

(56) References Cited

U.S. PATENT DOCUMENTS

| | | |
|---|---|---|
| 3,715,409 A | 2/1973 | Broughtn |
| 7,091,389 B1 | 8/2006 | Kato et al. |
| 8,008,536 B2 | 8/2011 | Winter et al. |
| 8,329,975 B2 | 12/2012 | Pieper et al. |
| 2009/0326308 A1 | 12/2009 | Kulprathipanja et al. |
| 2010/0305381 A1* | 12/2010 | Go ............... B01D 15/1835 585/826 |
| 2013/0153502 A1* | 6/2013 | Harris .......... B01D 15/1828 210/660 |
| 2014/0031601 A1 | 1/2014 | Porter |

OTHER PUBLICATIONS

Chementator: Boosting Ethylene Yield, Chemical Engineering, v107, n12, p. 19, Nov. 2000; ISSN: 00092460; Publisher: Chemical Week Associates.

* cited by examiner

*Primary Examiner* — Tam M Nguyen

(57) ABSTRACT

A simulated moving bed separator and methods for isolating a desired component are provided. A method includes removing a raffinate from a raffinate bed of a simulated moving bed separator. The raffinate includes an undesired component, and the simulated moving bed separator includes a plurality of adsorbent beds circularly coupled together, a distributor, and a plurality of conduits coupling the distributor to the plurality of adsorbent beds. The adsorbent beds include the raffinate bed, a desorbent bed, and a zone 4 flush bed positioned between the raffinate bed and the desorbent bed. Desorbent is added to the desorbent bed through a desorbent conduit. The zone 4 flush conduit is flushed to the desorbent conduit, where the zone 4 flush conduit is coupled to the zone 4 flush bed.

19 Claims, 4 Drawing Sheets

SIMULATED MOVING BED SEPARATORS AND METHODS FOR ISOLATING A DESIRED COMPONENT

TECHNICAL FIELD

The present disclosure generally relates to methods and apparatuses for isolating a desired component from a mixed feed, and more particularly relates to methods and simulated moving bed separators for isolating a desired component from a mixed feed using selective adsorption.

BACKGROUND

Selective adsorption can separate a desired component from a mixed feed by adsorbing the desired component while letting other components in the mixture flow by. The other components are referred to herein as "undesired components" to differentiate them from the desired component, but the undesired components may be used for other purposes or processes and therefore be desirable in their own right. An adsorption separator may use an adsorbent with a higher affinity for the desired component than for the undesired components in the mixture, so the desired component is adsorbed onto the surface and within the pores, cavities, or other areas of the adsorbent. The adsorbent may adsorb some of the desired component, the undesired components, and other compounds, but the more preferred compounds are adsorbed more readily. Selective adsorption can also proceed by adsorbing undesired components and allowing the desired component to flow through the adsorbent for collection. In this description, the desired component is adsorbed by the adsorbent, but this description is also applicable to embodiments where the undesired components are adsorbed and the desired component flows through the adsorbent.

As the mixture flows over the adsorbent, the desired component is adsorbed so the fluid passing through the adsorbent has a lower concentration of the desired component, and therefore a higher concentration of other components. This adsorption process diminishes after a period of time because the available adsorption sites on the adsorbent are taken up. The undesired components in the mixture may then be drained or displaced from the adsorbent in a purification process. Additional fluid flowing through the adsorption bed pushes the undesired components out in a raffinate stream. A desorbent may then be introduced into the adsorbent bed, where the desorbent flushes the desired component from the adsorbent. The desorbent displaces the desired component from the adsorbent in a desorption process, and the desired component can then be collected with some excess desorbent.

In a simulated moving bed separator, a plurality of adsorption beds filled with adsorbent are fluidly connected together and fixed in position. Some simulated moving bed separators use a plurality of adsorption beds fluidly coupled in a circular manner, so fluids flow through the adsorption beds in a loop. i.e., fluid flows from the first adsorption bed into the second adsorption bed, fluid flows from the second adsorption bed into the third adsorption bed, and so on, and fluid from the last adsorption bed flows into the first adsorption bed. The simulated moving bed separator has various zones separated by the inlet and outlet points. The zones shift through the simulated moving bed separator by changing inlet and outlet locations from one adsorption bed to the next. For example, the mixed feed may be introduced into a feed bed, a raffinate stream may be removed from a raffinate bed, the desorbent may be added to a desorbent bed, and the desired component may be removed from an extract bed in an extract stream. A plurality of conduits fluidly couple the adsorption beds to a distributor, and the distributor shifts or changes the feed bed, the raffinate bed, the desorbent bed, and the extract bed in what is referred to as a valve step. The valve step in a typical simulated moving bed separator changes the feed bed from one adsorbent bed to an adjacent adsorbent bed. The valve step also changes the raffinate bed, the desorbent bed, and the extract bed to directly adjacent adsorbent beds. After a period of time, the distributor changes the feed bed and the other named adsorbent beds again, such that each adsorption bed serves as the feed bed, the raffinate bed, the desorbent bed, and the extract bed in turn during what is referred to as a valve cycle.

Zone 4 is one of the zones described above, where zone 4 includes the adsorbent beds between the raffinate bed and the desorbent bed. Undesired components are removed from the simulated moving bed separator in the raffinate bed, and the desorbent is added to the simulated moving bed separator in the desorbent bed. Zone 1 includes the adsorbent beds between the raffinate bed and a feed bed, so fluid that does not exit the raffinate bed in the raffinate stream flows from zone 1 to zone 4. The circular fluid flow in zone 4, while still in the positive direction, is significantly slowed relative to other zones in order to control the residence time of contaminants that bypass the raffinate stream and cross from zone 1 into zone 4. Residence time in the adsorbent bed immediately below the raffinate bed should be sufficiently high so that the undesired components are not carried out of that adsorbent bed, and residence time is increased by slowing fluid flow. With sufficient residence time, the undesired components remain in the adsorbent bed immediately below the raffinate bed until the valve step, at which time the adsorbent bed immediately below the raffinate bed becomes the raffinate bed, and the undesired components can be washed out with the raffinate stream. If sufficient residence time in zone 4 is not maintained, contaminants will enter zone 3 and exit the simulated moving bed separator in the extract stream. This increases the quantity of undesired component in the extract, resulting in a less complete separation. Manipulating the flow rate in zone 4 typically involves increasing the rate at which the raffinate stream is removed from the raffinate bed (thus lowering the zone 4 flow rate and increasing the residence time in zone 4). To maintain overall balance, extra desorbent is added to the desorbent bedn with an increase in the raffinate stream flow rate. The extra desorbent added to the process is traditionally separated from the desired components and the undesired components by distillation, and more energy is required for the distillation when more desorbent is present.

The simulated moving bed separator simulates countercurrent movement of liquid and solid, where the solid is the adsorbent. In a true moving bed, solid adsorbent moving counter currently to liquid will carry some amount of liquid within the pores of the adsorbent. This "flow" of liquid suspended within the pores of the adsorbent is subtracted from the free liquid flow countercurrent to the adsorbent in order to arrive at a calculated "net" flow of liquid. Since the control equations of a true moving bed are the same as those of a simulated moving bed, those skilled in the art frequently refer to the liquid flow within zone 4 as negative. In other words, within zone 4 of a true moving bed, the flow of liquid suspended within the pores of the moving adsorbent may be greater than the flow of free liquid countercurrent to the adsorbent and thus produce a 'net' negative flow. Irrespective of net fluid flow and typical calculations, the actual free liquid flow within zone 4 should be sufficiently small to control resident time within zone 4. The flow of free liquid within zone 4 remains in the positive direction (the same direction as all other zones), even though conventional calculations based on a true moving bed predict a net negative flow in zone 4.

Accordingly, it is desirable to develop methods and apparatus to separate a desired component from a mixture with a lower concentration of undesired components in the extract. In addition, it is desirable to reduce the total amount of energy needed to recover the desired component and the undesired component while reducing the concentration of undesired components in the extract. Furthermore, other desirable features and characteristics of the present embodiment will become apparent from the subsequent detailed description and the appended claims, taken in conjunction with the accompanying drawings and this background.

BRIEF SUMMARY

Simulated moving bed separators and methods for isolating a desired component from a mixed feed are provided. In an exemplary embodiment, a method includes removing a raffinate from a raffinate bed of a simulated moving bed separator. The raffinate includes an undesired component, and the simulated moving bed separator includes a plurality of adsorbent beds circularly coupled together, a distributor, and a plurality of conduits coupling the distributor to the plurality of adsorbent beds. The adsorbent beds include the raffinate bed, a desorbent bed, and a zone 4 flush bed positioned between the raffinate bed and the desorbent bed. Desorbent is added to the desorbent bed through a desorbent conduit. The zone 4 flush conduit is flushed to the desorbent conduit, where the zone 4 flush conduit is coupled to the zone 4 flush bed.

In accordance with another exemplary embodiment, a method for separating a desired component from a mixed fee stream includes adding a desorbent to a desorbent bed of a simulated moving bed separator. The desorbent is added in a volume sufficient for desorbent to flow away from the desorbent bed in a positive direction into a zone 3 of the simulated moving bed separator, and the desorbent is added in sufficient volume to produce a net negative flow in to zone 4 of the simulated moving bed separator. The net negative flow of desorbent in zone 4 is increased by adding a zone 4 flush fluid to the desorbent, where the zone 4 flush fluid is from a zone 4 flush conduit.

In accordance with a further exemplary embodiment, a simulated moving bed separator includes a plurality of adsorbent beds fluidly coupled together in a circular manner, where the adsorbent beds include a raffinate bed, a desorbent bed, a feed bed, an extract bed, and a zone 4 flush bed. The simulated moving bed separator also includes a distributor and a plurality of conduits fluidly coupling the adsorbent beds to the distributor. The conduits include a raffinate conduit fluidly coupled to the distributor and to the raffinate bed, a desorbent conduit fluidly coupled to the distributor and to the desorbent bed, a feed conduit fluidly coupled to the distributor and to the feed bed, an extract conduit fluidly coupled to the distributor and to the extract bed, and a zone 4 flush conduit fluidly coupled to the distributor and to the zone 4 flush bed. The distributor is configured to introduce liquid from the zone 4 flush conduit into the desorbent conduit.

BRIEF DESCRIPTION OF THE DRAWINGS

Various embodiments will hereinafter be described in conjunction with the following drawing figures, wherein like numerals denote like elements, and wherein:

FIG. 3A is before a valve step, and FIG. 3B is after the valve step.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to methods and apparatuses for isolating a desired component from a mixed feed. Simulated moving bed separators are known in the industry, such as the simulated moving bed separator known by the trademark SORBEX® available from UOP, LLC of 25 East Algonquin Road, Des Plaines, Ill. 60016 U.S.A. A simulated moving bed separator includes a plurality of adsorbent beds, where a plurality of conduits fluidly couples the adsorbent beds with a distributor that controls the flows to and from the various adsorbent beds, as described above. Fluid is stagnant in several of the conduits that are not actively adding or removing fluid during a valve step. As the simulated moving bed separator advances through valve steps, a conduit that was used to add desorbent to the desorbent bed advances to a conduit in zone 4, so that conduit is full of desorbent. In some previous methods of operation, the desorbent within this conduit would remain stagnant for some valve steps, and then be removed from the simulated moving bed separator with the raffinate at a later stage. The desorbent from that conduit would then be separated from the raffinate by distillation and re-used in the simulated moving bed separator. This desorbent increases the total amount of desorbent added to the system. The desorbent within the conduit described above is flushed into a new conduit for the desorbent bed and thereby increases the total amount of desorbent added to the desorbent bed. The increased flow of desorbent into the desorbent bed is matched by decreasing free liquid flow in zone 4, and no adjustment of the raffinate stream flow is required. In terms of typical simulated moving bed calculations, zone 4 net flow becomes more negative. In this description, "net flow" is defined as the flow based on typical simulated moving bed calculations, that account for free liquid flow and liquid that is carried within the pores of the adsorbent, and the term "liquid flow" or "flow" without the word "net" refers to free liquid flow and does not include the liquid carried within the pores of the adsorbent. This increased net negative flow does not require the addition of more desorbent than would have otherwise been used, so the purity of the desired product can be increased without increasing the energy for distilling and recovering the desorbent.

Figure 1:
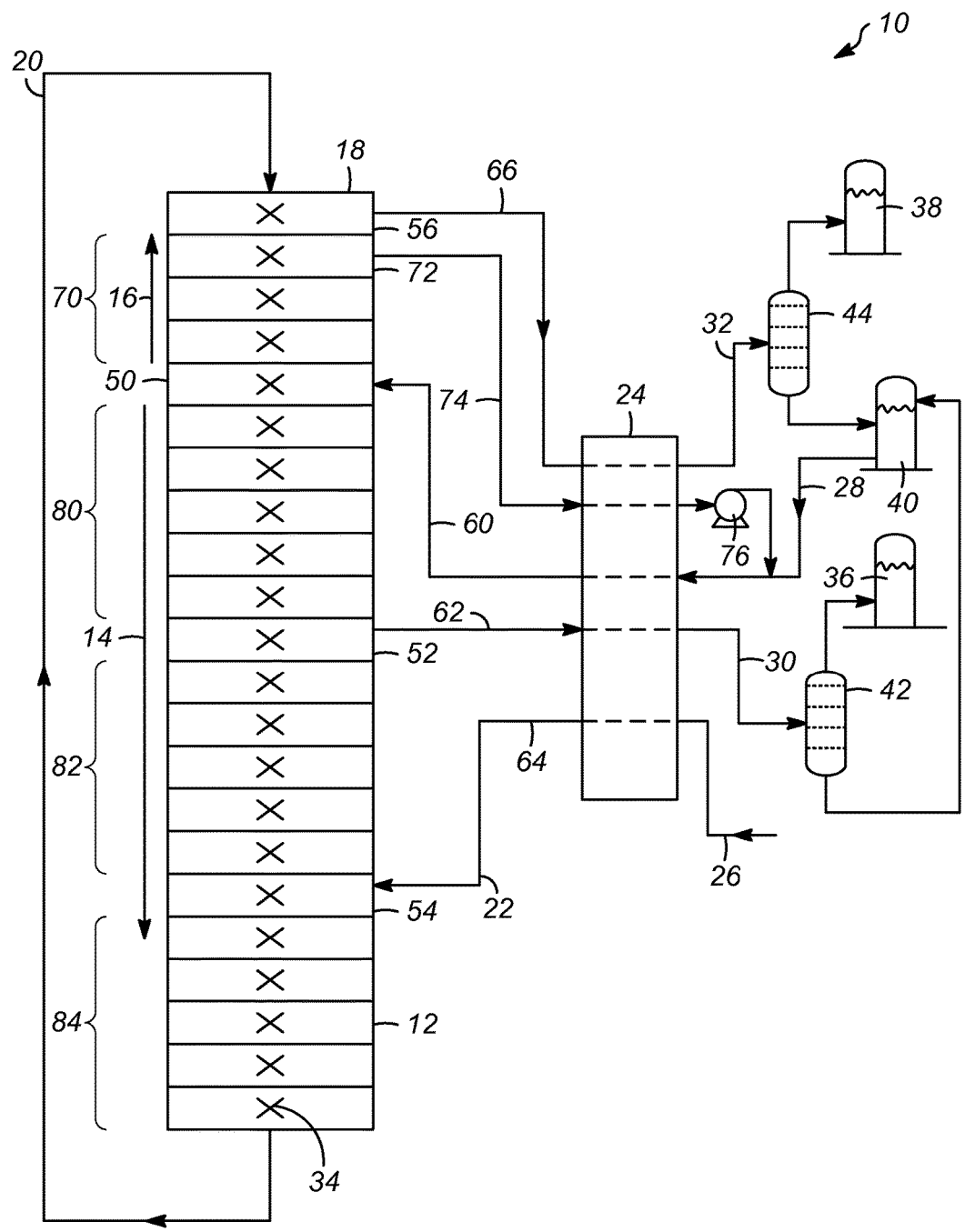
FIG. 1 is a schematic diagram of an exemplary embodiment of a simulated moving bed separator, where only the conduits for the mixed feed, desorbent, raffinate, extract, and zone 4 flush are illustrated.

Referring to an exemplary embodiment in FIG. 1, a simulated moving bed separator 10 includes a plurality of adsorbent beds 12 fluidly coupled together in a circular manner. Each adsorbent bed 12 receives fluid from an adjacent adsorbent bed 12, and each adsorbent bed 12 transfers fluid to a different adjacent adsorbent bed 12 with the exception of inlet or outlet adsorbent beds 12 that receive or discharge fluid from the simulated moving bed separator 10. As can be seen, there are two adsorbent beds 12 adjacent to any one other adsorbent bed 12, where the top and bottom adsorbent beds 12 are effectively adjacent because fluid flows directly from one to the other. The positive direction of fluid flow through the adsorbent beds 12 is represented by arrow 14, and a negative direction of flow is represented by arrow 16, wherein the positive direction 14 and the negative direction 16 are different from each other, and are opposite to each other with respect to the adsorbent beds 12. The adsorbent beds 12 may be connected in one continuous stack 18, as illustrated in FIG. 1, with a recirculation line 20 transporting fluid from the adsorbent bed 12 at the bottom of the stack 18 to the adsorbent bed 12 at the top of the stack 18, or from the adsorbent bed 12 at the top of the stack 18 to the adsorbent bed 12 at the bottom of the stack 18 in embodiments with upwards flow. Fluid generally flows through the adsorbent beds 12 in the stack 18, and is then recirculated from the last adsorbent bed 12 to the first adsorbent bed 12 by the recirculation line 20, so the flow is circular. In alternate embodiments, the adsorbent beds 12 may be in two or more stacks 18 with two or more recirculation lines 20 configured to carry fluid through the adsorbent beds 12 in a loop, as illustrated in the exemplary embodiment in FIG. 2. The stacks 18 may include one, two, or more adsorbent beds 12 in various embodiments, but the flow in the positive direction 14 is circular regardless of the number of stacks 18 in the simulated moving bed separator 10, with the exception of areas with net flow in the negative direction 16. In an exemplary embodiment, the flow of free liquid is in the positive direction 14 throughout the simulated moving bed separator 10.

Figure 2:
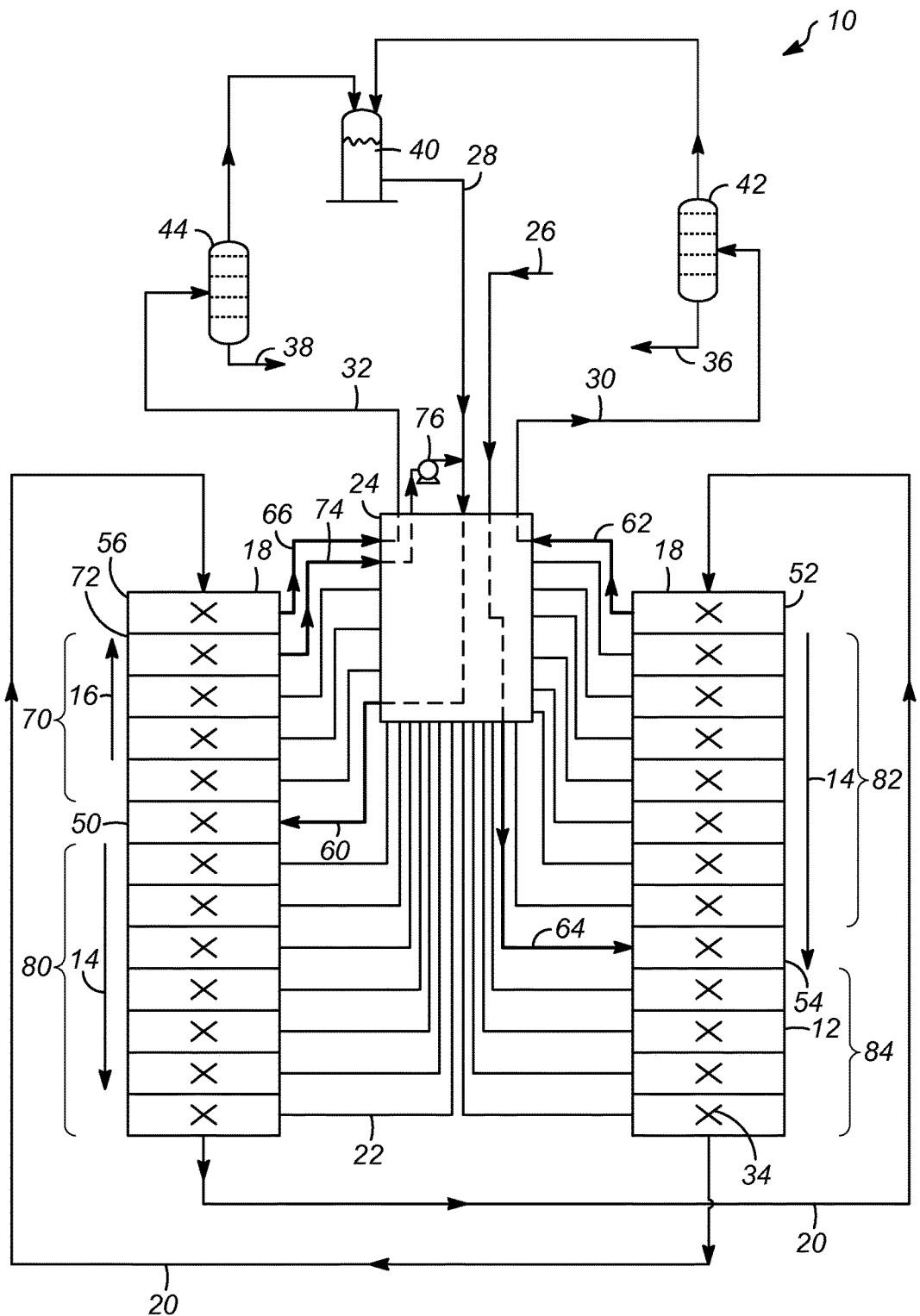
FIG. 2 is a schematic diagram of an alternate embodiment of a simulated moving bed separator with two stacks, where all the conduits are illustrated.

Referring to the embodiments illustrated in FIGS. 1 and 2, a plurality of conduits 22 fluidly couples the plurality of adsorbent beds 12 to a distributor 24. FIG. 1 illustrates conduits 22 with fluid flow, and FIG. 2 illustrates all the conduits 22, including those without any fluid flow, but it is understood that there is a conduit 22 to each adsorbent bed 12 in FIG. 1 despite not being illustrated to simplify the drawing. The distributor 24 moves the locations of the liquid input and output to the stack 18 by directing the appropriate fluid flow to the proper conduit 22, and therefore to the proper adsorbent bed 12. In some embodiments, the distributor 24 is a rotary valve, as is understood by those skilled in the art, but other types of distributors 24 can be used in alternate embodiments, such as a plurality of individual valves (not illustrated) that may be computer controlled. The conduits 22 have a volume, where the volume of the conduit 22 depends on the internal diameter and the length of the conduit 22. The distance between the distributor 24 and the various adsorbent beds 12 may vary from one adsorbent bed 12 to the next, so one or more of the conduits 22 may have a larger volume than others, and one or more conduits 22 will have the largest conduit volume. One or more of the conduits 22 will also have the smallest volume. In some embodiments, the conduits 22 all have essentially the same diameter, so the conduit 22 with the longest length between the distributor 24 and the adsorbent bed 12 will have the largest volume. However, in other embodiments, the conduits 22 may have different diameters. If all the conduits 22 have the same volume, that volume is both the largest and the smallest volume for the conduits 22.

The distributor 24 directs fluid flow through the conduits 22 to the input and output locations, or adsorbent beds 12 used for the input or output of fluids. After a specified time period, which is called the step time in some embodiments, the distributor 24 advances one index and redirects the inputs and outputs to the directly adjacent adsorbent bed 12 (in the positive direction 14) from the adsorbent bed 12 previously in use in what is called a valve step. When the adsorbent bed 12 used for an input or output has completed an entire loop of the stack 18 it is called a valve cycle, so each adsorbent bed 12 is used for each input and each output in one valve cycle. In many embodiments, there are at least two input streams and two output streams employed at any one time in the simulated moving bed separator 10, including a mixed feed stream 26, a desorbent stream 28, an extract stream 30, and a raffinate stream 32. The locations at which the mixed feed stream 26 and the desorbent stream 28 enter the simulated moving bed separator 10 and the extract stream 30 and the raffinate stream 32 leave the simulated moving bed separator 10 are simultaneously shifted in the same direction by the distributor 24. Each shift in location of these input or output points delivers or removes liquid from a different adsorbent bed 12 within the simulated moving bed separator 10.

In many embodiments, the volume of the plurality of adsorbent beds 12 is about constant, such as within about 5% of an average adsorbent bed volume, and the step time for each valve step is also about constant. In alternate embodiments, the volume of the adsorbent beds 12 varies from one adsorbent bed 12 to the next, and the step time may vary during a valve cycle. In an exemplary embodiment with a constant step time and adsorbent bed volume, the step time is about 60 to about 90 seconds, but in other embodiments the step time is about 15 minutes to about an hour, and other step times are also possible.

The adsorbent beds 12 include an adsorbent 34, and the type of adsorbent 34 varies depending on the use of the simulated moving bed separator 10. In an exemplary embodiment, the simulated moving bed separator 10 is used to separate para-xylene as a desired component 36 from a mixed xylene stream, where ortho-xylene, meta-xylene and ethylbenzene are undesired components 38. As mentioned above, ortho-xylene, meta-xylene, and ethylbenzene have many beneficial uses and are valuable, so the reference to ortho-xylene, meta-xylene, and ethylbenzene as undesirable components 38 is merely to distinguish them from the desired component 36, and not to disparage the value of ortho-xylene, meta-xylene, and ethylbenzene. In embodiments where the desired component 36 is para-xylene, the adsorbent 34 may be a zeolitic material that preferentially adsorbs para-xylene over meta-xylene, ortho-xylene, and ethylbenzene. In another embodiment where the desired component 36 is meta-xylene, the adsorbent 34 is a zeolitic material that preferentially adsorbs meta-xylene over para-xylene, ortho-xylene, and ethylbenzene. In yet another embodiment, the simulated moving bed separator 10 is used to separate olefins from paraffins where the desired component 36 is olefins, and the adsorbent 34 is a zeolitic material that preferentially adsorbs olefins over paraffins. In still another embodiment, the simulated moving bed separator 10 is used to separate normal paraffins from branched paraffins where the desired component 36 is normal paraffins, and the adsorbent 34 is a zeolitic material that preferentially adsorbs normal paraffins over branched paraffins. Many other uses and adsorbents 34 are possible in various embodiments, such as the separation of pharmaceutical materials, enzymes or other biological materials, or a wide variety of compounds. In various embodiments, the adsorbent 34 is activated charcoal, silica gel, ion-exchange resins, or many other materials.

The extract stream 30 includes the extract, where the extract includes the desired component 36 and the desorbent 40 from the desorbent stream 28. In an exemplary embodiment, the extract is about 50 mass percent or more desorbent 40, and about 50 mass percent or less desired component 36, but in alternate embodiments the extract is about 20 to about 80 mass percent desorbent 40 and about 80 to about 20 mass percent desired component 36. The extract stream 30 is transferred to an extract distillation column 42 to separate the desired component 36 from the desorbent 40. The extract stream 30 may be stored, such as in a tank, drums, tote bins, or other containers (not illustrated) before distillation, but the extract stream 30 flows directly to the extract distillation column 42 in some embodiments. In an exemplary embodiment, the desired component 36 is para-xylene and the desorbent 40 is toluene, but in other embodiments the desorbent 40 can be diethyl benzene or other compounds. When the desorbent 40 is toluene, the desorbent 40 has a lower boiling point than the desired component 36, para-xylene, so the toluene is vaporized and lifted in the extract distillation column 42. Lifting the desorbent 40 requires energy, so the lower the concentration of toluene in the extract stream 30, the less energy required to recover a set quantity of the desired component 36. In embodiments where the desorbent 40 has a higher boiling point than the desired component 36, the desired component 36 is lifted in the extract distillation column 42, but the desorbent 40 is still heated and processed so higher concentrations of desorbent 40 still increase the energy required in the extract distillation column 42. The desorbent 40 is re-used in the simulated moving bed separator 10 in many embodiments, and the desired component 36 is removed from the system.

The raffinate stream 32 is transferred to a raffinate distillation column 44 in a similar manner as the extract is transferred to the extract distillation column 42. The raffinate stream 32 is separated into the desorbent 40 and the undesired component 38 by distillation, similar to the separation for the extract. As with the extract, the desorbent 40 may be more or less volatile than the undesired component 38. For example, the desorbent 40 toluene is less volatile than the undesired components 38 ortho-xylene, meta-xylene and ethylbenzene, and the desorbent 40 diethyl benzene is less volatile than ortho-xylene, meta-xylene and ethylbenzene. The same energy considerations apply to the raffinate distillation column 44 as the extract distillation column 42 described above.

In an exemplary embodiment, the desorbent 40 from the desorbent stream 28 is introduced to the stack 18 in a desorbent bed 50, where the desorbent bed 50 is one of the adsorbent beds 12. The extract is removed from the stack 18 in an extract bed 52, where the extract bed 52 is one of the adsorbent beds 12 in the positive direction 14 from the desorbent bed 50. The extract includes the desired component 36 and the desorbent 40 used to flush the desired component 36 out of the adsorbent 34. The mixed feed stream 26 is introduced to the stack 18 in a feed bed 54, where the feed bed 54 is in the positive direction 14 from the extract bed 52, and the raffinate stream 32 is removed from the stack 18 in a raffinate bed 56 in the positive direction from the feed bed 54. The mixed feed includes the desired component 36 and the undesired component 38 to be separated, and the raffinate includes the undesired component 38 and the desorbent 40 used to flush the undesired component 38 out of the adsorbent 34. A desorbent conduit 60, an extract conduit 62, a feed conduit 64, and a raffinate conduit 66 are conduits 22 that fluidly couple the desorbent bed 50, the extract bed 52, the feed bed 54, and the raffinate bed 56, respectively, to the distributor 24.

Fluid flows in the positive direction 14 from the desorbent bed 50 to the extract bed 52, from the extract bed 52 to the feed bed 54, and from the feed bed 54 to the raffinate bed 56. Free liquid flows in the positive direction 14 from the desorbent bed 50 to the raffinate bed 56 to complete the loop within the stack 18, but the net flow from the desorbent bed 50 to the raffinate bed 56 is in the negative direction 16 in some embodiments. With each valve step, the desorbent conduit 60, the extract conduit 62, the feed conduit 64, and the raffinate conduit 66 change, along with the associated adsorbent beds 12. Some conduits 22 may be flushed and therefore have fluid flow, but most of these flushes are not illustrated in FIG. 1 to simplify the illustration.

The adsorbent beds 12 between the raffinate bed 56 and the desorbent bed 50 is referred to as zone 4 70 of the simulated moving bed separator 10. Zone 3 80 includes the adsorbent beds 12 between the desorbent bed 50 and the extract bed 52, zone 2 82 includes the adsorbent beds 12 between the extract bed 52 and the feed bed 54, and zone 1 84 includes the adsorbent beds 12 between the feed bed 54 and the raffinate bed 56. As mentioned above, net fluid flow is in the negative direction 16 in zone 4 70, but free liquid fluid flow is in the positive direction 14.

In an exemplary embodiment, only one extract stream 30 is removed from the stack 18 at a time, so all the extract being removed from the stack 18 at one time has essentially the same composition. In an alternate embodiment, there is only one feed bed 54 in the stack 18 at any one time, so all the mixed feed is added to the stack 18 in the same feed bed 54. In an alternate embodiment, there is only one mixed feed stream 26 introduced to the stack 18 at any one time.

A zone 4 flush bed 72 is coupled to the distributor 24 by a zone 4 flush conduit 74. A zone 4 flush fluid (that includes desorbent 40) within the zone 4 flush conduit 74 is flushed away from the zone 4 flush bed 72 to the distributor 24, and added to the desorbent conduit 60 to increase the amount of desorbent 40 added to the desorbent bed 50. The distributor 24 is configured to direct the zone 4 flush fluid from the zone 4 flush conduit 74 into the desorbent conduit 60. A zone 4 pump 76 may be used to pressurize the zone 4 flush fluid to facilitate addition to the desorbent conduit 60, so the zone 4 flush fluid is pumped into the desorbent conduit 60 in some embodiments. The zone 4 flush bed 72 is within zone 4 70, so the zone 4 flush bed 72 is between the raffinate bed 56 and the desorbent bed 50. In an exemplary embodiment, the zone 4 flush bed 72 is directly adjacent to the raffinate bed 56, as illustrated, but the zone 4 flush bed 72 may be another adsorbent bed 12 within zone 4 70 in alternate embodiments.

In an exemplary embodiment, a zone 4 flush volume is about the same as the largest conduit volume, such as within about 5% of the largest conduit volume, where the zone 4 flush volume is the amount of zone 4 flush fluid flushed into the desorbent conduit 60. In an alternate embodiment, the zone 4 flush volume is about the same as the volume of the zone 4 flush conduit 74, such as within about 5% of the volume of the zone 4 flush conduit 74, regardless of whether the zone 4 flush conduit 74 is the conduit 22 with the largest volume or not. The distributor 24 and other components of the simulated moving bed separator 10 may be configured with a constant zone 4 flush volume, and that volume can be set to be about the same as the largest conduit volume so the zone 4 flush conduit 74 is essentially completely flushed for every valve step in a valve cycle. In an alternate embodiment, the zone 4 flush volume is adjusted to match the volume of the zone 4 flush conduit 74 for each adsorbent bed 12 serving as the zone 4 flush bed 72. In this embodiment, the zone 4 flush volume changes with each valve step that utilizes a zone 4 flush conduit 74 with a different volume than the previous zone 4 flush conduit 74. In yet another embodiment, the zone 4 flush volume may be about the same (within about 5%) as a minimum conduit volume, where the minimum conduit volume is the volume of the conduit 22 with the smallest volume. A zone 4 flush volume with a minimum conduit volume may help minimize or prevent flushing of undesired component from the zone 4 flush bed 72 into the desorbent bed 50.

Figure 3A:
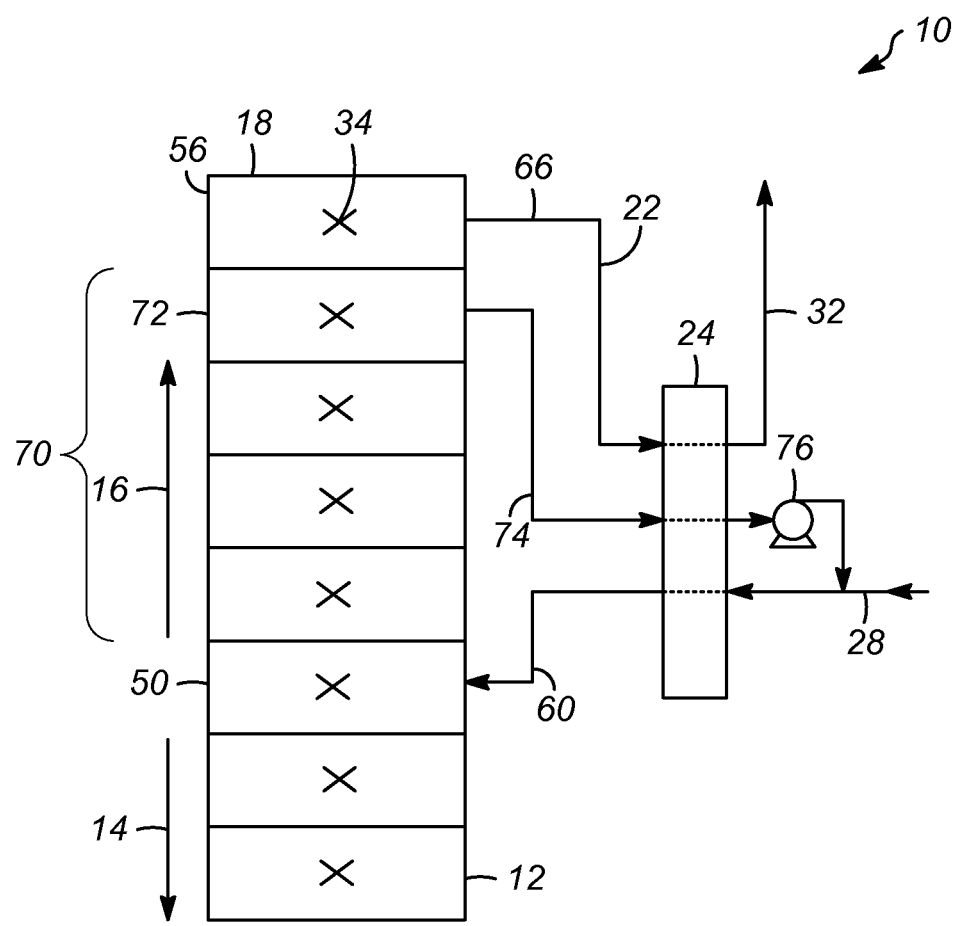
FIGS. 3A and 3B are schematic diagrams of an exemplary embodiment of a portion of a simulated moving bed separator, where
Figure 3B:
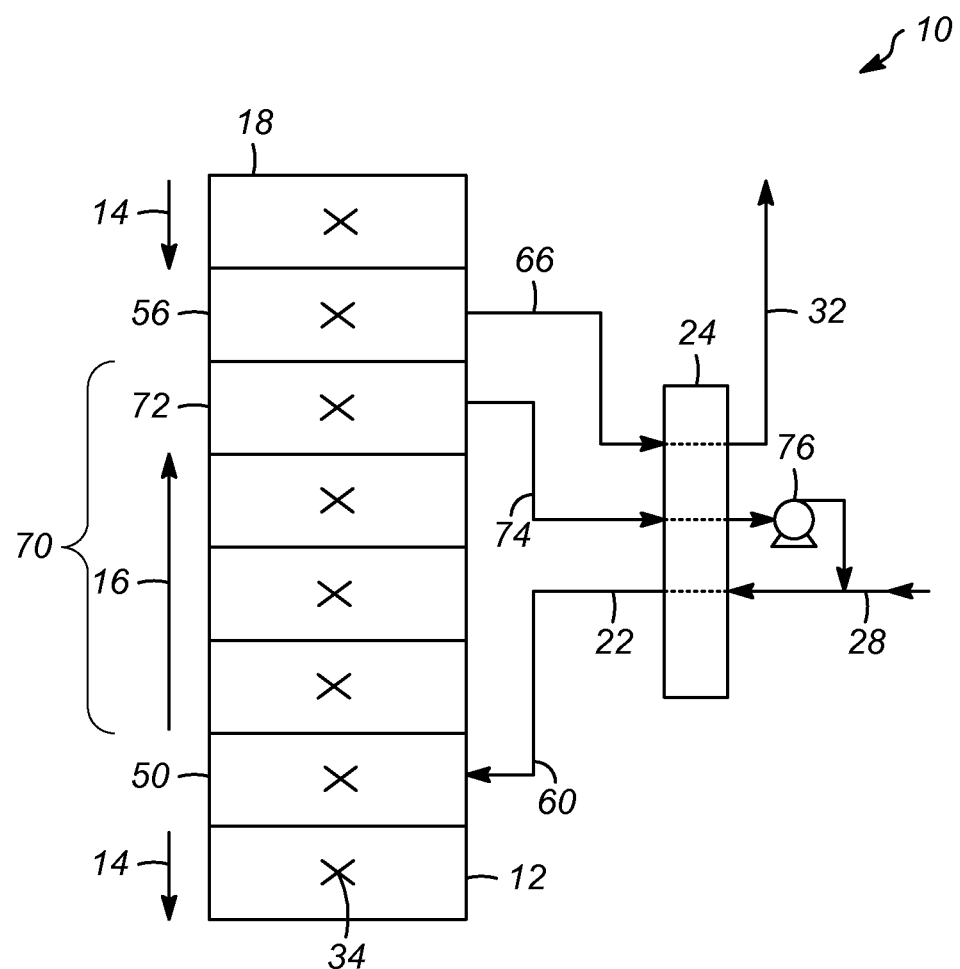

Referring to the exemplary embodiment illustrated in FIGS. 3A and 3B, with continuing reference to FIGS. 1 and 2, the inputs and outputs to the stack 18 are shifted in the positive direction 14 to the adjacent adsorbent bed 12 in a valve step, where FIG. 3A illustrates selected inputs and outputs before the valve step, and FIG. 3B illustrates the selected inputs and outputs after the valve step. The desorbent bed 50, the raffinate bed 56, and the zone 4 flush bed 72 are each shifted to the adjacent adsorbent bed 12 in the positive direction 14 during the valve step. The conduits 22 going to several of the adsorbent beds 12 are not in use, so the fluid within them remains stagnant during one or more valve steps. Therefore, the last fluid flow through the zone 4 flush conduit 74 was desorbent when it was the desorbent conduit 60 during a previous valve step. As such, the zone 4 flush conduit 74 remains full of desorbent (the last material that flowed through it.) For example, the zone 4 flush fluid is about 98 mass percent or greater desorbent 40 in some embodiments. Material from the zone 4 flush bed 72 flows into the zone 4 flush conduit 74 during the flushing process, so some of the material from zone 4 70 is left in the zone 4 flush conduit 74 after the flush.

With one or more valve steps, the conduit 22 that was the zone 4 flush conduit 74 advances to become the raffinate conduit 66. As such, the material from zone 4 that remains in the zone 4 flush conduit 74 is added to the material in the raffinate. The desorbent 40 in the zone 4 flush conduit 74 (the zone 4 flush fluid) would have been added to the raffinate if the zone 4 flush did not occur. As such, the flush of the zone 4 flush conduit 74 diverts desorbent 40 that would otherwise have been added the raffinate to the desorbent bed 50, and thereby increases the flow of desorbent 40 added to the desorbent bed 50. The material removed from zone 4 70 during the zone 4 flush balances the increase of desorbent 40 and no change in flow rate of the raffinate stream 32 is required. Undesired components 38 that flowed from the zone 4 flush bed 72 remain in the zone 4 flush conduit 74, and are captured in the raffinate stream 32 after one or more valve steps. In some embodiments, the zone 4 flush bed 72 is changed into the raffinate bed 56 in a valve step, and the undesired components 38 that are in what was the zone 4 flush bed 72 and/or the zone 4 flush conduit 74 before the valve step are removed from what has become the raffinate bed 56 after the valve step. The undesired components 38 are removed from the raffinate bed 56 in the raffinate stream 32. As material is removed from the zone 4 flush bed 72 for the zone 4 flush, the free liquid flow in zone 4 70 decreases and the residence time within zone 4 70 increases. As such, the zone 4 flush increases the net negative flow (in the negative direction 16) in zone 4 70. Increased net negative flow in zone 4 70 tends to wash more of the undesired component 38 from zone 4 70 into the raffinate stream 32 (after one or more valve steps) and thereby decreases the undesired component 38 in the extract stream 30. The decreased undesired component 38 in the extract stream 30 increases the purity of the desired component 36 recovered from the extract distillation column 42. Therefore, the flush of the zone 4 flush conduit 74 into the desorbent conduit 60 increases the concentration of the recovered desired component 36 without the use of additional desorbent 40 and the higher energy usage associated with additional desorbent 40.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

What is claimed is:

1. A method of separating a desired component from a mixed feed, the method comprising the steps of:
    removing a raffinate from a raffinate bed of a simulated moving bed separator, wherein the raffinate comprises an undesired component, wherein the simulated moving bed separator comprises a plurality of adsorbent beds circularly coupled together, a distributor, and a plurality of conduits fluidly coupling the distributor to the plurality of adsorbent beds, and wherein the plurality of adsorbent beds comprises the raffinate bed, a desorbent bed, and a zone 4 flush bed positioned between the raffinate bed and the desorbent bed;
    adding a desorbent to the desorbent bed through a desorbent conduit; and
    flushing a zone 4 flush conduit to the desorbent conduit, wherein the zone 4 flush conduit is fluidly coupled to the zone 4 flush bed.

2. The method of claim 1 wherein flushing the zone 4 flush conduit comprises flushing the zone 4 flush conduit wherein the zone 4 flush bed is directly adjacent to the raffinate bed.

3. The method of claim 1 wherein flushing the zone 4 flush conduit comprises increasing a net negative flow in the zone 4.

4. The method of claim 1 further comprising:
    changing the zone 4 flush bed to the raffinate bed in a valve step; and
    removing the undesired component from the raffinate bed.

5. The method of claim 1 further comprising:
    removing an extract from an extract bed of the simulated moving bed separator, wherein the plurality of adsorbent beds comprise an adsorbent, wherein the adsorbent is a zeolitic adsorbent that preferentially adsorbs para-xylene over meta-xylene, ortho-xylene, and ethylbenzene, and wherein the desired component is para-xylene.

6. The method of claim 1 further comprising:
    removing an extract from an extract bed of the simulated moving bed separator, wherein the plurality of adsorbent beds comprise an adsorbent, wherein the adsorbent is a zeolitic adsorbent that preferentially adsorbs meta-xylene over para-xylene, ortho-xylene, and ethylbenzene, and wherein the desired component is para-xylene.

7. The method of claim 1 further comprising:
    removing an extract from an extract bed of the simulated moving bed separator, wherein the plurality of adsorbent beds comprise an adsorbent, wherein the adsorbent is a zeolitic adsorbent that preferentially adsorbs normal paraffins over branched paraffins, and wherein the desired component is normal paraffins.

8. The method of claim 1 further comprising:
removing an extract from an extract bed of the simulated moving bed separator, wherein the plurality of adsorbent beds comprise an adsorbent, wherein the adsorbent is a zeolitic adsorbent that preferentially adsorbs olefins over paraffins, and wherein the desired component is olefins.

9. The method of claim 1 further comprising:
adding the mixed feed into a feed bed of the simulated moving bed separator, wherein the mixed feed comprises the desired component and the undesired component.

10. The method of claim 9 wherein adding the mixed feed comprises adding the mixed feed, wherein the mixed feed comprises ortho-xylene, meta-xylene, and para-xylene, and wherein para-xylene is the desired component.

11. The method of claim 1 further comprising:
introducing the mixed feed into a feed bed of the simulated moving bed separator, wherein the mixed feed comprises the desired component and the undesired component; and
removing an extract from an extract bed of the simulated moving bed separator, wherein the extract comprises the desorbent and the desired component; and wherein:
fluid flows from the feed bed toward the raffinate bed in a positive direction;
a net fluid flow from the desorbent bed is toward the raffinate bed in a negative direction different than the positive direction;
fluid flows from the desorbent bed towards the extract bed in the positive direction; and
fluid flows from the extract bed toward the feed bed in the positive direction.

12. The method of claim 1 wherein flushing the zone 4 flush conduit comprises flushing the zone 4 flush conduit with a flush volume, wherein the flush volume is within about 5% of a volume of a largest conduit volume.

13. The method of claim 1 wherein flushing the zone 4 flush conduit comprises flushing the zone 4 flush conduit with a flush volume, wherein the flush volume is within about 5% of a volume of the zone 4 flush conduit.

14. The method of claim 1 wherein flushing the zone 4 flush conduit comprises pumping fluid from the zone 4 flush conduit into the desorbent conduit.

15. The method of claim 1 wherein flushing the zone 4 flush conduit comprises flushing a zone 4 flush fluid from the zone 4 flush conduit, wherein the zone 4 flush fluid comprises about 98 mass percent or more desorbent.

16. A method of separating a desired component from a mixed feed, the method comprising the steps of:
adding a desorbent to a desorbent bed of a simulated moving bed separator, wherein the desorbent is added in a volume sufficient for the desorbent to flow away from the desorbent bed in a positive direction into a zone 3 of the simulated moving bed separator, and the desorbent is added in sufficient volume to produce a net negative flow in a zone 4 of the simulated moving bed separator; and
increasing the net negative flow of the desorbent in the zone 4 by adding a zone 4 flush fluid to the desorbent, wherein the zone 4 flush fluid is from a zone 4 flush conduit.

17. The method of claim 16 wherein increasing the net negative flow in the zone 4 comprises adding the zone 4 flush fluid to the desorbent, wherein the zone 4 flush fluid is about 98 mass percent or greater desorbent.

18. The method of claim 16 further comprising:
adding the mixed feed to a feed bed of the simulated moving bed separator, wherein the mixed feed comprises the desired component and an undesired component;
removing an extract from an extract bed of the simulated moving bed separator, wherein the extract comprises the desired component and the desorbent;
removing a raffinate from a raffinate bed, wherein the raffinate comprises the desorbent and the undesired component; and
reducing a concentration of the undesired component in the extract by increasing the net negative flow of the desorbent in the zone 4.

19. The method of claim 16 further comprising:
changing a zone 4 flush bed to a raffinate bed in a valve step, wherein the zone 4 flush bed is coupled to the zone 4 conduit; and
removing an undesired component from the raffinate bed.

* * * * *